United States Patent [19]

Wilkes

[11] Patent Number: 5,026,279
[45] Date of Patent: Jun. 25, 1991

[54] DENTAL ARTICULATOR

[76] Inventor: Dutch B. Wilkes, P.O. Box 1250, Bartow, Fla. 33830-1250

[21] Appl. No.: 466,608

[22] Filed: Jan. 17, 1990

[51] Int. Cl.⁵ .................. A61C 11/00; A61C 19/00
[52] U.S. Cl. ............................. 433/60; 433/57; 433/54; 433/74
[58] Field of Search .............. 433/57, 58, 59, 60, 433/61, 54, 55, 56, 62, 63, 64, 65, 66, 67, 74, 53

[56] References Cited

U.S. PATENT DOCUMENTS

| | | | |
|---|---|---|---|
| 1,644,106 | 10/1927 | Bridge | 433/60 |
| 2,611,961 | 9/1952 | Neer | 433/60 |
| 4,382,787 | 5/1983 | Huffman | 433/64 |

FOREIGN PATENT DOCUMENTS 349758  4/1937  Italy .................. 433/66

Primary Examiner—John J. Wilson
Assistant Examiner—Cindy A. Cherichetti
Attorney, Agent, or Firm—John S. Hale

[57] ABSTRACT

A dental articulator for use with a dental stone comprising; a lower jaw member and an upper jaw member mounted to the lower jaw member. One of said jaw members is provided with a pivot post and a key member and the other jaw member defines a apertre which fits around the pivot post and a key way which selectively receives the key member for positioning the jaw members in a selected fixed positional relationship. A plurality of slots are formed in each jaw member to give the jaw member flex in the vertical and lateral direction and serrations are formed in the end of each jaw member to prevent rotation out of the dental stone. A dowel holding rod with associated dowel pins mounted thereto is mounted to the ends of each jaw member for mounting in selective jaw casts in one embodiment of the invention.

19 Claims, 3 Drawing Sheets

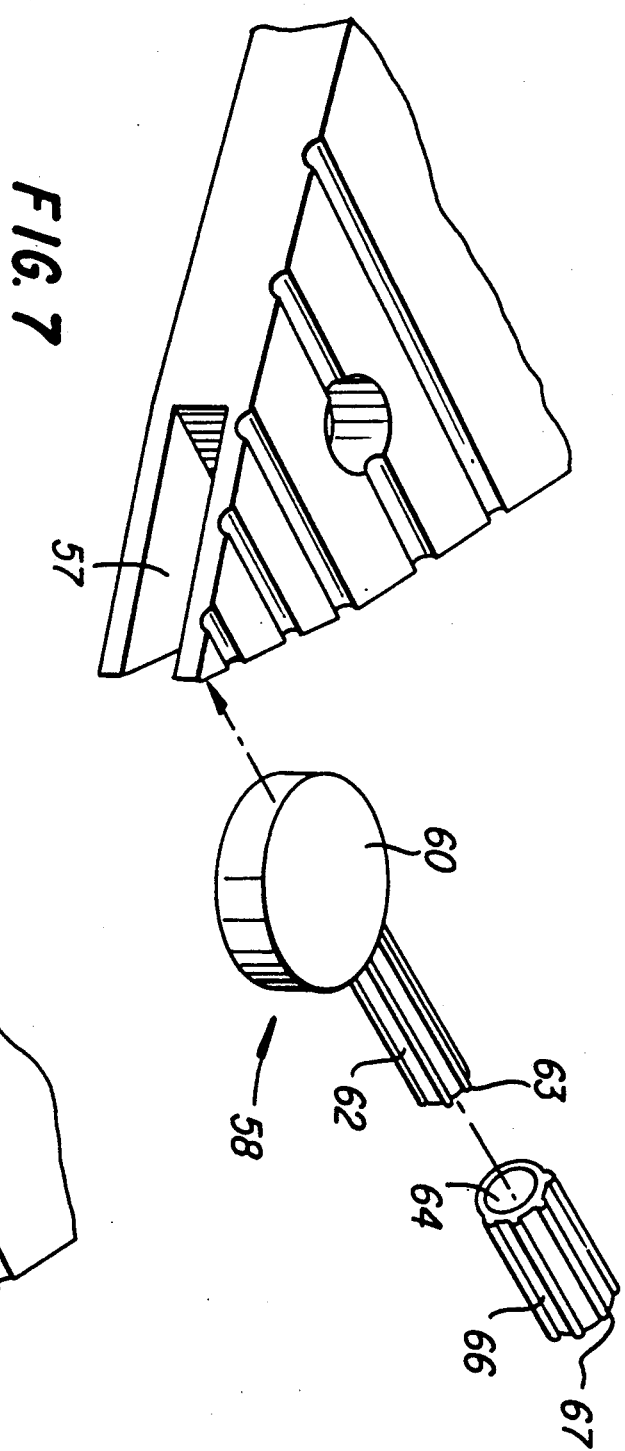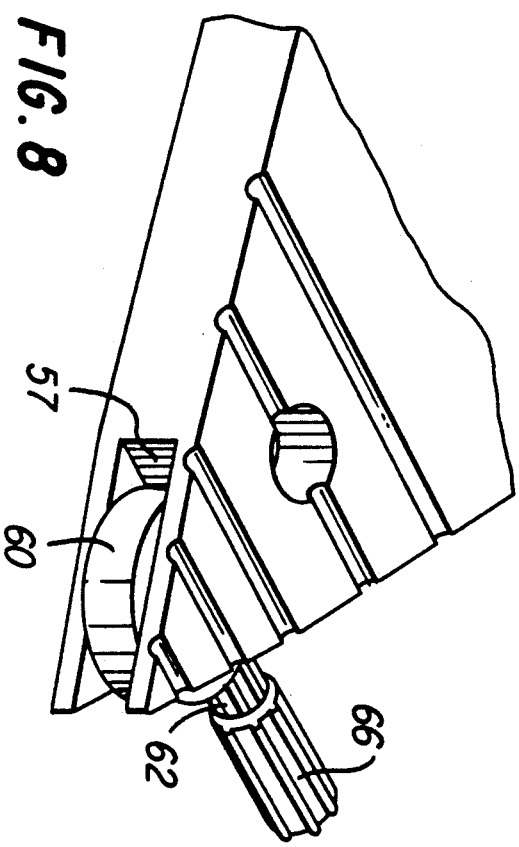

DENTAL ARTICULATOR

FIELD OF THE INVENTION

The invention is generally related to a dental device and more particularly it relates to a dental articulator for use with a dental model comprising casts of a set of upper teeth and a set of lower teeth of a person.

BACKGROUND OF THE INVENTION

Dental articulators are used in conjunction with models or casting in developing prosthodontic dental appliances. In typical applications, a dentist will make an impression of the patients mouth and utilize this impression to cast a model. The model is then mounted on an articulator to insure that the cap, crowns, bridges or dentures are sized and shaped to correctly fit in alignment with the remaining piece in the patients mouth. Dental technicians initially fabricate the model and then mount the model on the dental articulator for final finishing and fitting steps.

It is necessary to support such models in a relatively natural hinge relationship so as to mimic as closely as possible the biting movements. If the prosthodontic appliances are not properly shaped, a patient will be forced to undergo multiple adjustments which could possibly damage his or her teeth. It should be noted that a natural bite involves many motions in addition to the up and down motion as the human jaw is capable of side to side and back and forth motions.

It is an important feature that a dental articulator permit the ready separation of the components of dental models while allowing for their realignment in proper registration. Thus it is necessary for dental technicians to perform detailed work on prosthodontic appliances mounted onto dental articulators which requires that the articulator permit model separation. Such model separation will improve the quality of the prosthodontic appliance as well as decrease the quantity of time taken for its production and the attenuate costs inherent therewith.

There is a wide variety of dental articulators and various degrees of sophistication presently available.

There have been many attempts for a number of years to solve the problem of accurately and inexpensively using an articulator for use with a dental model. Such articulator range from simple devices affording only fixed pivotal movement between a pair of casts to complex devices which simulate the full range of occlusal and masticatory registrations unique to the dental patient. General speaking, the simple devices are generally inadequate to provide accurate registered prosthetic restoration requiring frequent trips for adjustment while the complex devices are difficult to operate and require extensive training to use properly.

U.S. Pat. Nos. 4,734,033; 4,533,323; 4,449,930 and 4,382,787 disclose embodiments of a dental model articulators which comprise a pair of substantially U-shaped brackets having limbs which are pivotally interconnected through the use of snap-fit pivot fasteners.

In these embodiments, spherical members are formed integrally with cross-pieces of each of the U shaped brackets and a mounting member is provided for attachment to each cast. Each mounting member defines a socket in the rear portion within which the spherical member of one of the brackets fits to form a ball and socket joint.

A problem with this type of construction is that two adhesive bonds have to be formed for each cast; namely the bonding of the mounting member to the cast and the bonding of the spherical member in the socket. Furthermore, while the adhesive bonds are setting, the casts together with the articulator have to be held increasing a likelihood that the position of the articulator relative to the casts is moved during setting of the adhesive bonds. In addition with the provision of the snap fit type interconnection between the limbs of the brackets, lateral movement without the snap fit interconnections coming apart is limited.

U.S. Pat. No. 4,786,253 discloses a dental model articulator including two portions connected by a flexible hinge with ends of the portions having a socket and, spherical member for attachment in a semi-spherical cavity formed in the rear surface of the upper and lower teeth casts.

U.S. Pat. No. 4,797,097 discloses a dental articulator having a pair of attachment members, each of which is adapted to be mounted to a dental casting with a lockable ball joint attachment having one end formed with pins which are inserted into the cast. Likewise U.S. Pat. No. 3,916,524 discloses the use of pins which are inserted into bushing cast into the jaw molds. U.S. Pat. No. 4,319,875 shows a detachable fastener for joining impressions of a mouth onto a dental articulator using spherical members mounted in an articulator platform with the spherical portion of each member being mounted in a socket housing formed in the upper and lower jaw casts.

U.S. Pat. No. 4,207,677 discloses a dental model articulator with an upper jaw member and an intermediate connecting member having an over the center toggle type hinge and each jaw member being formed with a centrally disposed slot so as to leave a narrow passage or slit formed to receive a rib of the dental model mounting plate, thus facilitate positioning of the plate.

In addition various other hinged articulators of interest are shown by U.S. Pat. Nos. 4,439,151: 4,371,339: 4,263,715: 4,252,253: 3,510,947 and 2,697,279.

SUMMARY OF THE INVENTION

The present novel inexpensive articulator apparatus is adapted for disposable use with a dental model comprising cast of a set of upper teeth and a set of lower teeth of a person. The articulator includes a moveably mounted lower jaw member and an upper jaw member mounted by embedment or glued to slots cut in the dental cast. Slots are formed in each jaw member to give the member flex in the vertical and lateral direction and serrations are formed on the ends of each jaw member to prevent rotation out of the dental stone holding the cast of the set of upper and lower teeth of a person. Holes are placed in the distal end of each jaw member to hold a dowel rod holder which can be inserted into the dental stone and a hole is placed in each jaw member to hold an eight gauge plastic bar one-quarter inch long to prevent pull out. Alternately, the ends of each jaw member can be slotted to hold a securing assembly to the dental stone.

The present hovel articulator properly sets all posterior dowel pins so they are all parallel and in a correct position and gets away from the twin or double hinge type articulator. The single hinge of the present invention will lock into a working position yet unlock and separate when so desired in a non-working position. Furthermore in approximately eighty percent (80%) of the dental cases, the present invention can reduce to three steps a complex and expensive procedure for producing the die.

The slots in the articulator along with the plastic rod can be incorporated with wet dental stone which makes it possible for production dental laboratories to use it in situations where drying the cast is not economically possible. It is therefore seen that the present invention has a potential for using it to set dowel pins, particularly in the check bite impression. This is in an area needing maximum protection along with the single hinge and joint principle.

The present inventive articulator also has the ability to have vertical and lateral spring flex plus a maximum surface area for gluing in place.

A primary object of the articulator is to provide a normal occlusal and masticatory relationship of the dental casts with adequate flexibility to allow reproduction of normal chewing functions.

In the accompanying drawings, there is shown an illustrative embodiment of the invention from which these and other of objectives, novel features and advantages will be readily apparent.

BRIEF DESCRIPTION OF THE DRAWINGS

FIG. 7 is an enlarged exploded perspective view of an alternate embodiment of the end of the articulator apparatus shown in FIG. 1; and FIG. 8 is an enlarged perspective view of an assembled alternate embodiment of the end of the articulator apparatus shown in FIG. 7.

DETAILED DESCRIPTION OF THE DRAWINGS

Figure 1:
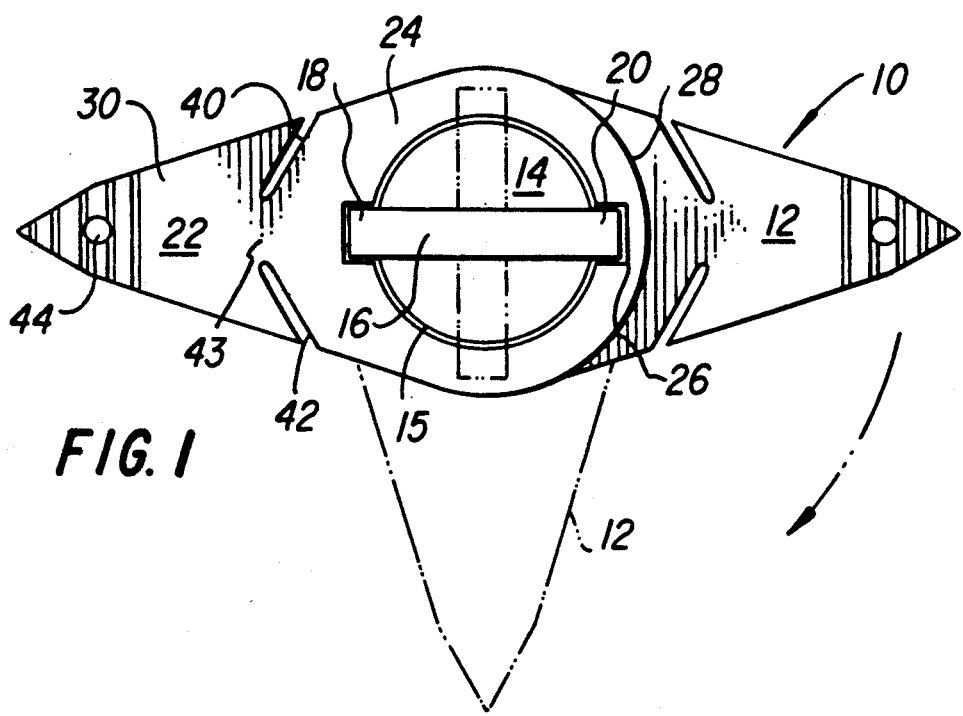
FIG. 1 is a side elevational view of the inventive articulator apparatus showing movement of one jaw with respect to the other jaw in phantom.
Figure 2:
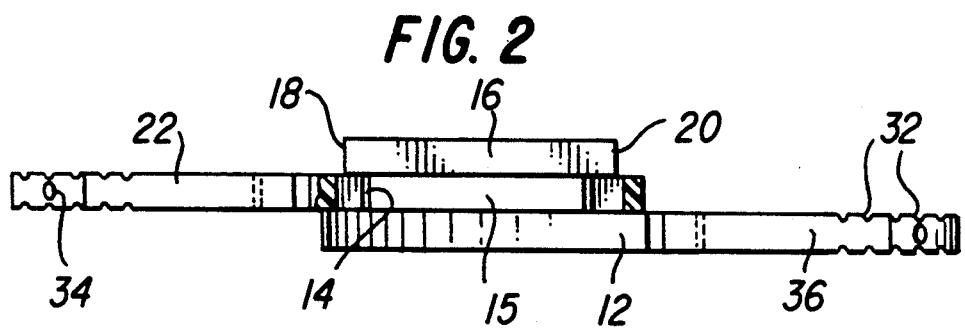
FIG. 2 is a top plan view of the articulator apparatus partially in section shown in FIG. 1.
Figure 6:
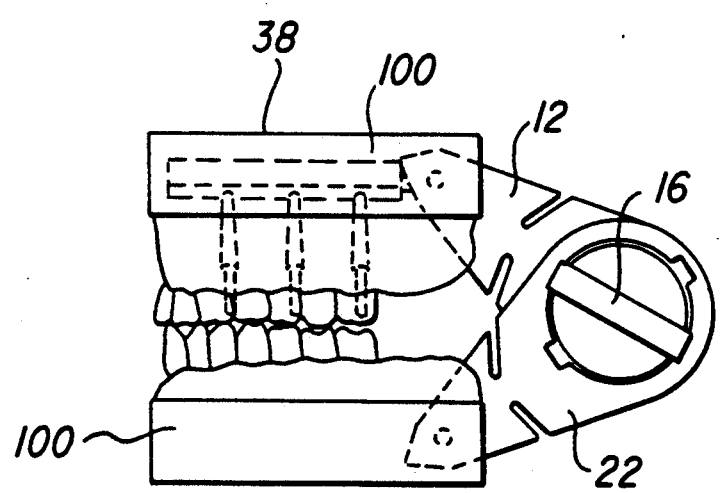
FIG. 6 is a side elevational view of the assembly of FIG. 5 showing location of the dowel pin holder in the jaw member in phantom.

The best mode and preferred embodiment of the invention is shown in FIGS. 1 through 6. As shown in FIGS. 1, 2 and 6 a multipiece articulator 10 is shown with hinged dental stone engaging jaw members 12 and 22. Each of the jaw members is constructed of plastic material, such as polypropylene, polyethylene, or the like approximately 3 mm in thickness. Jaw member 12 has an integral circular pivot post 14 centrally extending from one end with a key member 16 mounted to and extending outwardly from the top surface of pivot post 14. The key member 16 is bar shaped with ends 18 and 20 both of which extend past the outer wall surface of 15 of the circular pivot post 14.

Figure 3:
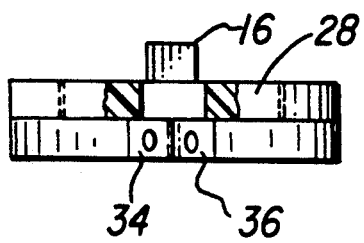
FIG. 3 is a front elevational view taken from the right hand side of the articulator apparatus of FIG. 1 with the rear section of the jaw partially broken away.
Figure 4:
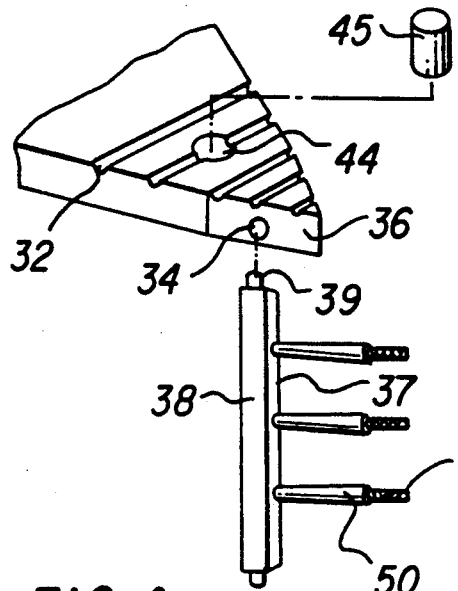
FIG. 4 is an enlarged perspective view of a portion of the end of the articulator apparatus shown in FIG. 1 with an exploded optional dowel pin holder and pin.
Figure 5:
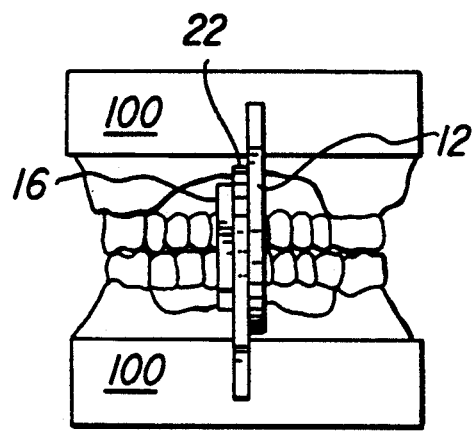
FIG. 5 is a front elevational view of the articulator apparatus mounted in the dental stone cast of upper and lower teeth.

A second jaw member 22 of the same general outline configuration as jaw member 12 is provided with a throughgoing circular aperture 24 therein having a diameter which is slightly greater than the diameter of the circular pivot post 14 and a rectangularly shaped key way 26 which is configured to allow key member 16 to pass therethrough. The throughgoing aperture 24 is defined by a wall of jaw member 22 having a thickness substantially equal to the height of pivot post 14 allowing the lower surface of key member 16 to slidably frictionally engage the upper surface 23 of engagement member 22. The rectangular keyway 26 has slightly greater dimension then the key member 16. Thus the keyway, key member, pivot post and circular aperture form a hinge mechanism which will lock into the working position yet unlock and separate when so desired in the non working position. The basic shape of each of the jaw members 12 and 22 is the same with the back end of jaw member 22 being slightly narrower from back to front to prevent it locking if dental stone touches the front edge. The proximal end 28 of both jaw members 12 and 22 is rounded and the other distal end 30 is arrow head shaped. Each arrow head shaped end 30 forms an acute angle at its distal point and is provided with a plurality of parallel serrations 32 to prevent rotation out of the dental stone. Angularly positioned cylindrical blind bores 34 are centrally drilled in sides 36 of the distal end 30 as shown in FIGS. 2-4. Thus each end of the articulator engagement member would have a small round blind bore 34 positioned on each side of the end 30, so that when the two jaw halves are together in a working relationship, the top forward hole would be 53 millimeters from the bottom edge of the other articulator half. These blind bores have a 0.3 millimeter diameter adapted to receive and hold dowel pin holding plastic rods 38 (see FIG. 4) mounted into the dental stones 100 (see FIG. 6). The dowel pin holding rod end 39 is friction fit into the blind bore 34 of the articulator and allows rotation of the dowel pin holding rod in the bore 34 for the desired orientation of the dowel pins 50 mounted on the holding rod 38. Dowel pins 50 with beveled ends 52 are used to hold the ends into the dental stone. The dowel pin holding rod 38 is preferably 45 millimeters long and has multiple holes 37 as close together as possible to allow maximum flexibility for using dowel pins 50 where needed. The dowel pin holding rod 38 holds the dowel pins 50 by friction. The dowel pin holder can be of several pin types and each permanent die base type that would lock the base stone or the die and permit a solid one piece pour to be sawed down through to the plastic and separated.

Each end 30 is provided with opposing through going slots 40 and 42 approximately one half inch deep which leaves approximately three millimeters of plastic material 43 between the slots 40 and 42. This three millimeter small area 43 as shown in FIG. 1 provides flex in the vertical and horizontal direction to simulate the chewing motions of human dentition.

For a check bite impression where both upper and lower jaws are impressioned in one tray, the non-working side is poured first and the lower articulator member 12 has an eight gauge one-quarter inch long plastic rod 45 press fitted by hand into bore 44. The rod 45 is embedded in the poured stone so that it can be inverted on the bench and the top of the upper jaw member 22 is placed so that it points straight up the middle of the impression. The dowel pin holder rod 38 is inserted and the holes 37 are visually aligned. The holes that get pins are marked with a pencil or other marking means. The dowel pins 50 are placed in the holes and verified. The working dies are then poured and the top of the articulator with the dowel pin holder holding the dowel pins is closed to the proper depth. A base is added to cover the dowel pins and incorporate the top articulator member. Thus the size, shape and position of the articulator allows the articulator dental professional to trim the case on the model trimmer after it is articulated.

FIGS. 7 and 8 shows an alternate embodiment of the distal ends of jaw members 12 and 22 as shown in the previous figures. In this embodiment a slot 57 is cut in the end of each jaw member to receive part 58. Part 58 which is glued in slot 57 comprises a circular base 60 with a shaft 62 extending from the base. The shaft is formed with ridges 63 which serve as vent grooves for glue extrusion when shaft 62 is cemented inside the bore 64 of ridged shaft 66. The shaft 62 fits into the bore 64 of ridged shaft 66 so that it can be glued into position in it. The shaft 66 has ridges 67 to provide a rotational resistance in the dental stone as well as preventing it from being pulled out of the dental stone. Shaft 66 can be embedded in the heel or back end of the dental stone through either drilling a hole in the dental stone or embedding it in the soft dental stone before it sets up. Alternatively the shaft 66 could be picked up from a preformed base mold sometimes used in creating the base of the dental models.

Thus the construction shown in FIGS. 7 and 8 represent an almost universal joint type of connection when used on each distal end of jaws 12 or 22. Almost any configuration of models could be mounted up very quickly and securely using a standard diameter drill to drill one hole in the back of each cast 100 and inserting and cementing shaft 66, then placing the circular base 60 of part 58 into the slot 57 and aligning shaft 62 with bore 64 in shaft 66. Glue is applied to shaft 62 and it is inserted in bore 64 after which glue is applied to base 60 in slot 57.

Also a preformed rubber base can be used for making the bases for upper and lower casts 100 and the casts modified to hold shaft 66 in the correct relative position so that the base stone of the model secures it in position. Then when the cast is separated from the mold the base 60 is held in slot 57 on each end of the articulator while glue was applied to shaft 62 and shaft 62 is inserted in bore 64 of shaft 66. As previously noted the ridges 63 of shaft 62 allow excess glue to extrude out of the bore of shaft 66 during the cementing.

The light weight and simplicity of the function would allow a dental technician working on a dental appliance on this articulator the flexibility to quickly disassemble the parts for grinding and polishing procedures plus quick reassembling for checking these procedures.

In conjunction with the pivotal motion of the jaw members 12 and 22 functioning as a hinge to open and close they also have a section in each arm marked 43 in FIG. 1 that provides an area of flexibility in the vertical and lateral direction that presents a natural range of occlusal functions ideal for building crown and bridge work and other dental appliances. The ease of opening and separating the upper and lower articulating jaw members 12 and 22 without swapping of jerking permits easy realignment of the dental casts thus allowing the technician to quickly separate the cast so he or she has to hold only the one which he or she is working on directly.

In the foregoing description, the invention has been described with references to a particular preferred embodiment, although it is to be understood that the specific details may be carried out in other ways without departing from the true spirit and scope of the following details.

What I claim is:

1. An articulator apparatus for orienting the upper dental cast and the lower dental cast to each other for building dental appliances such as crown and bridge work comprising a cast engaging jaw member; a unitary hinge means mounted to said cast engaging jaw member, a second cast engaging jaw member rotatably mounted on said unitary hinge means and detachable from said unitary hinge means, said unitary hinge means comprising a key member secured on said first cast engaging jaw member and a keyway defined by the second cast engaging jaw member and removable cast engaging means mounted on the distal end of each jaw member to engage respective dental casts, said jaw members of said articulator apparatus engaging a dental cast by wet embedment in the initial pour of dental stone, each jaw member's distal end defining an arrow shaped heat of a thickness defining a width surface in turn defining bore means and locking serrations, said bore means receiving a rod means which extends from the width surface to form a mechanical wedge for embedment in wet dental stone.

2. An articulator apparatus as claimed in claim 1 wherein said rod means comprises a plastic rod holding a plurality of dowel pins.

3. An articulator apparatus as claimed in claim 1 wherein said distal end has throughgoing slot means cut therein.

4. An articulator apparatus as claimed in claim 1 wherein said distal serrated end further defines at least one blind bore adapted to receive anchoring means.

5. An articulator apparatus as claimed in claim 4 wherein said anchoring means is a dowel rod with means to hold a plurality of dowel pins.

6. An articulator apparatus as claimed in claim 5 wherein said dowel pins have bevelled ends.

7. A support assembly for supporting dental models comprising a articulator with an upper articulation tongue member and a lower articulation tongue member pivotally mounted to each other by a single pivotal post and aperture assembly, one of said articulation tongue members being provided with a post and the other articulation tongue member defining an aperture which receives said post, each articulator tongue member defining an arrow head shaped serrated end with opposing inwardly running slot means allowing flexure in the vertical and lateral direction and shaft holding means, said shaft holding means being engageable with a connecting mass of self hardening material in which the gum portion of a dental model is embedded so that upon hardening of the connecting mass, a unitary structure is constituted.

8. A dental articulator for use with a dental stone comprising; a lower jaw member, an upper jaw member pivotally mounted to said lower jaw member, slot means formed in each jaw member to give the jaw member flex in the vertical and lateral direction, serration means formed in the end of each jaw member to prevent rotation out of the dental stone, said serration means comprising a plurality of grooves cut into said jaw member substantially perpendicular to a line drawn through the linear axis of each jaw member and dowel means mounted on each of said jaw members.

9. A dental articulator as claimed in claim 8 wherein one of said jaw members is provided with a pivot post and key means and the other jaw member defines a aperture which fits around said pivot post and a key way which selectively receives said key means for positioning said jaw members in a selected fixed positional relationship.

10. A dental articulator as claimed in claim 8 wherein each said jaw member has a rounded end and an arrowhead shaped end.

11. A dental articulator as claimed in claim 8 wherein said dowel means comprises a plurality of holes formed in the end of said jaw member.

12. A dental articulator as claimed in claim 11 wherein said plurality of holes comprises at least 2 holes oppositely angled towards each other having a diameter which will receive and hold dowel means.

13. A dental articulator as claimed in claim 12 wherein said dowel means comprises a dowel with a round beveled end and an angled conical end having a greater diameter at the base of the cone then the diameter of the round beveled end.

14. A dental articulator for use with a dental stone comprising; a lower jaw member, an upper jaw member pivotally mounted to said lower jaw member, slot means formed in each jaw member to give the jaw member flex in the vertical and lateral direction, serration means formed in the end of each jaw member to prevent rotation of the jaw member out of dental stone, and holding means positioned on each of said jaw member, said holding means comprising a slot cut in the end of said jaw member, a base member mounted in said slot and a shaft extending from said base member.

15. A dental articulator as claimed in claim 14 including a second shaft means mounted to dental stone and adapted to be mounted to said base member shaft.

16. A dental articulator as claimed in claim 15 wherein said second shaft means is ridged.

17. A dental articulator as claimed in claim 14 wherein said base member is round and said shaft is ridged.

18. A dental articulator for use with a dental stone comprising; a lower jaw member, an upper jaw member pivotally mounted to said lower jaw member, slot means formed in each jaw member to give the jaw member flex in the vertical and lateral direction, serration means formed in the end of each jaw member to prevent rotation out of the dental stone, and dowel means mounted on each of said jaw member, said dowel means comprising a rod with a plurality of holes adapted to receive dowel pins.

19. A dental articulator for use with a dental stone comprising; a lower jaw member, an upper jaw member pivotally mounted to said lower jaw member, slot means formed in each jaw member to give the jaw member flex in the vertical and lateral direction, serration means formed in the end of each jaw member to prevent rotation out of the dental stone and dowel means mounted on each of said jaw members, dowel means comprising a bore cut in the distal end of each jaw member parallel to the plane of the jaw member surface, and pin means secured to said bore, said pin means comprising a round base member and a shaft member extending from said base member.

* * * * *